United States Patent

Goehde

[11] Patent Number: 5,861,094
[45] Date of Patent: Jan. 19, 1999

[54] FILTER FOR BIOLOGICAL PARTICLE SEPARATION

[76] Inventor: Wolfgang Goehde, Otto-Hahn-Strasse 32, 48161 Münster, Germany

[21] Appl. No.: 837,378

[22] Filed: Apr. 17, 1997

[51] Int. Cl.⁶ .............................. B01D 63/08; B01D 29/05
[52] U.S. Cl. .......................... 210/232; 210/472; 210/482; 210/474; 210/321.75; 210/321.84; 422/101
[58] Field of Search ...................................... 210/232, 238, 210/474, 482, 469, 321.84, 321.75, 472; 422/101; 436/178

[56] References Cited

U.S. PATENT DOCUMENTS

| | | |
|---|---|---|
| 4,769,145 | 9/1988 | Nakajima . |
| 5,043,082 | 8/1991 | Hermann . |
| 5,096,575 | 3/1992 | Cosack . |
| 5,240,861 | 8/1993 | Bieri . |

FOREIGN PATENT DOCUMENTS 2077132   12/1981   United Kingdom .

Primary Examiner—Thomas M. Lithgow
Attorney, Agent, or Firm—Walter C. Farley

[57] ABSTRACT

A biological particle filter has an upper body with an interior chamber for receiving a suspension to be filtered, the upper body having a central axis and a lower end with a bottom surface lying in a tilted plane forming an angle of between about 75° and about 85° with the central axis. A lower body has a chamber for receiving the lower end and bottom surface of the upper body with an upwardly facing annular support surface. The upwardly facing support surface lies in a plane parallel with said bottom surface. A passage extends downwardly below the screen for carrying away filtered suspension. An air inlet passage extends generally radially in at an upper end of the downwardly extending passage. A filter screen is between the bottom surface and the upwardly facing support surface and lies in a plane parallel with the tilted plane of the bottom surface, the tilted plane and the air passage promoting flow of filtered suspension through and away from the filter.

3 Claims, 2 Drawing Sheets

FILTER FOR BIOLOGICAL PARTICLE SEPARATION

FIELD OF THE INVENTION

This invention relates to a specialized filter for use in laboratory applications, particularly for separation of biological particles.

BACKGROUND OF THE INVENTION

In many fields of laboratory work, filters are used for separation of particles having different diameters. As an example of such filter use, in medicine (oncology, pathology or hematology), human tissue biopsies are taken in order to investigate a patient's biochemical and cytochemical properties. For many such investigations, single cell suspensions are produced by mechanical or enzymatic treatment. These procedures result in more or less homogeneous single cellular suspensions. Often larger particles, cell aggregates or small tissue pieces cannot be avoided. Such contaminations are usually removed by filtration of the suspension through filters with the appropriate mesh diameter, allowing only isolated single cells to pass.

There are numerous filters on the market. In one of these, upper and lower volumes are divided by a filter membrane (usually nylon mesh). The complete filter is put on top of a sample container such as a reagent glass. The suspension is pipetted into the upper volume and is intended to pass through the nylon mesh.

In many applications, such as preparation of single cell suspensions from tumors, very small suspension volumes need to be processed. For this purpose, special small filters for small volumes have been made.

The disadvantages of such filters are, first, that the lower volume becomes filled and this part of the suspension does not flow out of the filter because the wet filter membrane does not permit air to enter; and, second, if very small volumes are filtered (volumes smaller than the volume of the lower part of the filter), the suspension may fail to pass entirely through the filter mesh, either staying above the filter membrane or hanging as a drop from the under-surface of the filter membrane.

SUMMARY OF THE INVENTION

Accordingly, an object of the present invention is to provide a filter which is more uniformly effective in filtering suspensions for medical analytical use and can handle small quantities of suspension as well as assuring free flowing thereof.

Briefly described, the invention comprises a biological particle filter with an upper body having an interior chamber for receiving a suspension to be filtered and a lower body. The upper body has a central axis and a lower end with a bottom surface lying in a tilted plane forming an angle of between about 75° and about 85° with the axis. The lower body has a chamber for receiving the lower end and bottom surface of the upper body including an upwardly facing annular support surface with an opening therethrough. The upwardly facing support surface lies in a plane parallel with the bottom surface. A passage extends downwardly below the screen for carrying away filtered suspension, and a generally radially extending air inlet passage joins the upper end of the downwardly extending passage. A filter screen is between the bottom surface and the upwardly facing support surface so that the filter screen lies in a plane substantially parallel with the tilted plane of the bottom surface, the tilted plane and air passage promoting flow of filtered suspension through and away from said filter.

BRIEF DESCRIPTION OF THE DRAWINGS

In order to impart full understanding of the manner in which these and other objects are attained in accordance with the invention, a particularly advantageous embodiment thereof will be described with reference to the following drawings, which form a part of this disclosure, and wherein.

DESCRIPTION OF THE PREFERRED EMBODIMENT

Figure 1:
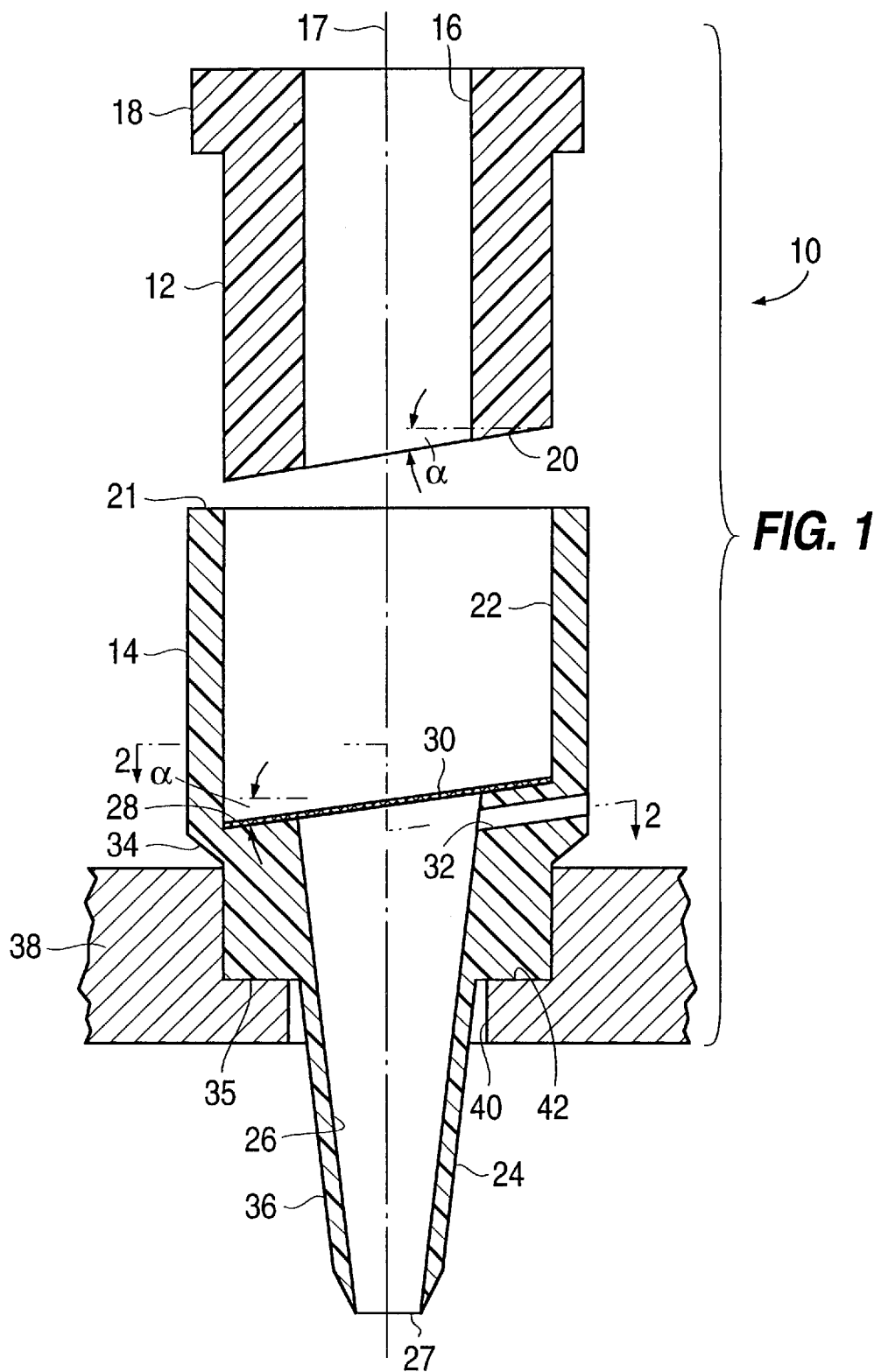
FIG. 1 is an exploded side elevation, in section, of a filter in accordance with the invention.

Referring first to FIG. 1, a filter 10 in accordance with the invention includes an upper, generally cylindrical portion 12 and a lower portion 14. Upper portion 12 has a central, interior cylindrical chamber 16 having a central axis 17, this chamber defining a volume to receive a suspension to be filtered. A flange 18 is formed at the upper end of portion 12 to limit insertion depth and to provide a means for engaging the upper portion for extraction and handling.

In this context, it will be recognized that terms such as "upper", "lower", "above" and "below" have important significance because the filter of the invention, as with other filters for similar purposes, are intended to operate under the force of gravity with the components thereof in a vertical orientation, i.e., with axis 17 substantially vertical.

Portion 12 has a lower end terminating in a bottom surface 20 which is not perpendicular to axis 17. Instead, surface 20 lies in a tilted plane which makes an angle a of between about 5° and about 15° with a plane perpendicular to axis 17 as shown in FIG. 1; or, stated differently, surface 20 lies in a plane making an angle of (90°−α) with the central axis, which would be between about 75° and 85°.

Figure 3:
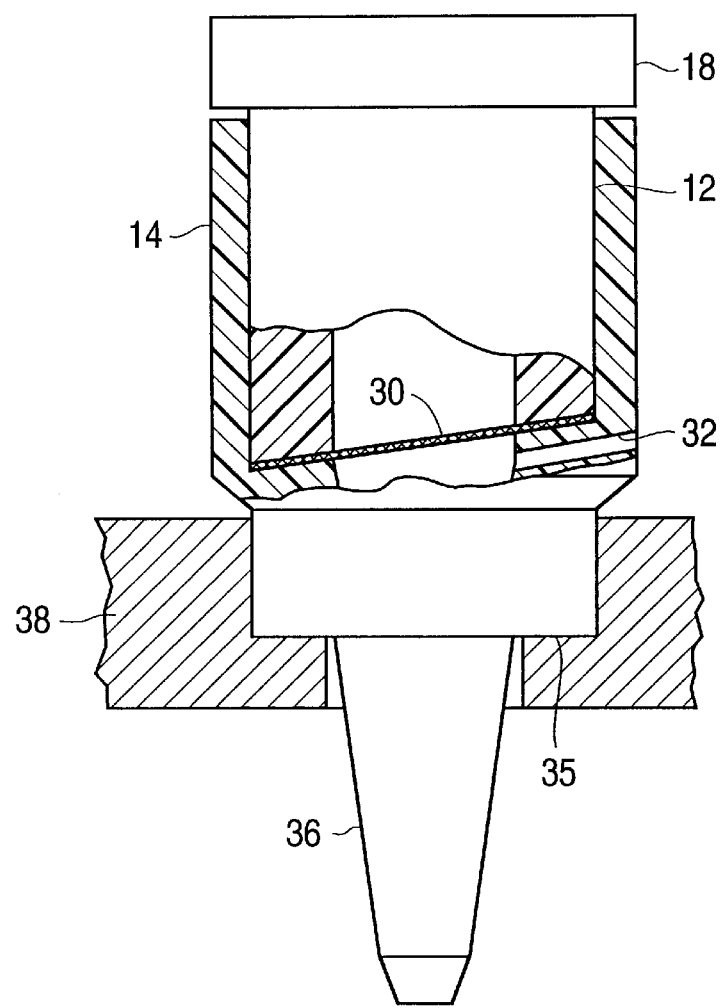
FIG. 3 is an assembled side elevation, partially in section, of the filter of FIG. 1.

Lower portion 14 has a cylindrical upper wall 21 the inner surface of which defines a chamber 22 comprising means for receiving the lower end and bottom surface of portion 12 as shown in FIG. 3. The central axis of chamber 22 is coaxial with axis 17. A wall 24 having a conical inner surface 26 extends downwardly below chamber 22. The upper end of surface 26 has a diameter substantially equal to the inner diameter of chamber 16 and smaller than that of chamber 22, leaving an upwardly facing peripheral support surface or shoulder 28. Shoulder 28 lies in a tilted plane which is substantially parallel with surface 20, forming the same angle with the central axis as plane 20. Conical surface 26 is also coaxial with chamber 22 and terminates at a bottom opening 27.

A screen or filter membrane 30 of a suitable mesh or opening size to perform the desired filtering process is supported on shoulder 26. Screen 30 is typically a nylon mesh screen. When the upper and lower portions of the filter are assembled as shown in FIG. 3, screen 30 is held between surface 20 and shoulder 28 of the filter portions.

Figure 2:
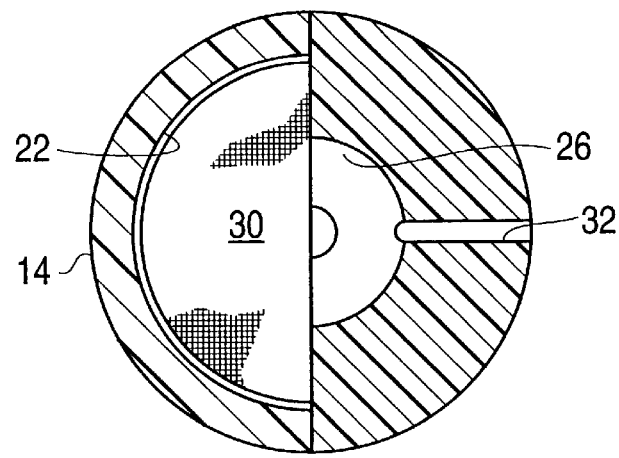
FIG. 2 is a transverse sectional view along line 3—3 of FIG. 1.

An air passage 32 extends generally radially inwardly from an outer surface of portion 14. Passage 32 opens to the outside of portion 14 and opens into the upper end of the conical volume defined by surface 26 just below shoulder 26 and screen 30, as also seen in FIG. 2. Passage 32 is cylindrical and its central axis preferably lies in a plane parallel with surface 20 and shoulder 26 so that it inner end is lower than its outer end.

The outer surface of portion 14 is formed with a beveled surface 34, a shoulder 35 and a tapered surface 36, any or all of which can be used to support the filter. In the embodiment shown, a support plate 38 has a vertical opening 40 with a recess forming an upwardly facing support shoulder 42 against which shoulder 35 rests. However the support plate is shown only for completeness and is not per se part of the present invention.

In use, a suspension to be filtered is injected into chamber 16 by pipetting or any conventional technique, the intention being for the liquid of the suspension and particles below a selected size to pass through the openings of screen 30. In filters of the prior art, the suspension closes the very small holes in the screen by adhesion and tends to remain at the screen. With hole 32, air is permitted to enter and the cell suspension flows downwardly out of opening 27 into a suitable receptacle, not shown.

The angle α of the screen permits the suspension to flow toward the lowest part of the screen. A pressure formed by the suspension column above this lowest point facilitates passage of the suspension beyond the filter screen. Thus, the combination of the sloping screen with the air passage guarantees that the suspension passes the screen.

Typically, the mesh has openings ranging in size from about 5 μm (micrometers) to about 1000 μm, depending upon the application, i.e., on the particles which are to be removed from the suspension. For cell extraction, the preferred range of sizes is between about 20 and 50 μm. The diameter of the upper part of the filter is about 12 mm and the total height of the filter is about 35 mm.

While one advantageous embodiment has been chosen to illustrate the invention, it will be understood by those skilled in the art that various modifications can be made therein without departing from the scope of the invention as defined in the appended claims.

What is claimed is:

1. A biological particle filter for separating particles from a liquid by gravity, the filter comprising:

an upper body having an interior chamber for receiving a suspension to be filtered, said upper body having a central axis and a lower end with a bottom surface, said bottom surface lying in a tilted plane forming an angle of between about 75° and about 85° with said axis, said central axis being vertical in use;

a lower body having
means for receiving said lower end and bottom surface of said upper body, said means for receiving including an upwardly facing support surface with an opening therethrough, said upwardly facing support surface lying in a plane parallel with said bottom surface,
means defining a downwardly extending passage below said support surface for carrying away filtered suspension, and
a generally radially extending air inlet passage at an upper end of said downwardly extending passage; and a filter screen between said bottom surface and said upwardly facing support surface, said filter screen lying in a plane substantially parallel with said tilted plane of said bottom surface, said tilted plane and said air passage promoting flow of filtered suspension through and away from said filter.

2. A filter according to claim 1 wherein said upper end of said downwardly extending passage comprises a frustoconical surface having a diameter substantially equal to said interior chamber of said upper body and a lower end with a smaller diameter.

3. A filter according to claim 2 wherein said upwardly facing support surface comprises an annular shoulder.

* * * * *